US00PP08296P

United States Patent [19]

Trees

[11] Patent Number: Plant 8,296

[45] Date of Patent: Jul. 6, 1993

[54] GERANIUM PLANT — BSR-100B DARK SALMON CULTIVAR

[75] Inventor: Scott C. Trees, Arroyo Grande, Calif.

[73] Assignee: George J. Ball, Inc., West Chicago, Ill.

[21] Appl. No.: 761,702

[22] Filed: Sep. 18, 1991

[51] Int. Cl.[5] ..... A01H 5/00

[52] U.S. Cl. ..... Plt./87.12

[58] Field of Search ..... Plt./87.12

[56] References Cited

U.S. PATENT DOCUMENTS

P.P. 7,926 7/1992 Hanes ..... Plt. 87.12

*Primary Examiner*—James R. Feyrer
*Assistant Examiner*—Elizabeth McElwain
*Attorney, Agent, or Firm*—Burns, Doane, Swecker & Mathis

[57] ABSTRACT

A new and distinct tetraploid *Pelargonium*×*hortorum* cultivar named BSR-100B Dark Salmon is provided. This new Zonal Geranium cultivar was the result of a controlled breeding program wherein the Tango cultivar (U.S. Plant Pat. No. 5,933) was pollinated by the Fidelio cultivar (U.S. Plant Pat. No. 5,752). The new cultivar forms attractive semi-double salmon florets which contrast well with dark green foliage which lacks zoning. The attractive dark green foliage coloration is well retained even during shipment. The growth habit is inherently compact and self-branching and does not require the use of growth regulators to maintain such growth characteristic. Good tolerance to wind and rain is exhibited.

4 Drawing Sheets

SUMMARY OF THE INVENTION

The present invention comprises a new and distinct Geranium cultivar, botanically known as *Pelargonium*-×*hortorum*, and hereinafter is referred to by the cultivar name BSR-100B Dark Salmon.

The new cultivar is the product of a planned breeding program which had as its objective the creation of a highly productive new Geranium cultivar which exhibits attractive blossoms, dark green foliage, a compact self-branching growth habit, no requirement for the use of a growth regulator, a propensity for rapid rooting, and stable foliage coloration during shipment. This objective was satisfactorily fulfilled in the cultivar of the present invention.

The breeding program which resulted in the production of the new cultivar of the present invention was carried out in a controlled environment during 1988 at Santa Maria, Calif., U.S.A. The female parent (i.e., the seed parent) was the TANGO cultivar (U.S. Plant Pat. No. 5,933). Such female parent formed semi-double red florets, and formed dark green foliage. The male parent (i.e., the pollen parent) was the Fidelio variety (U.S. Plant Pat. No. 5,752). Such male parent formed semi-double medium salmon florets, and formed medium green foliage. The parentage of the new cultivar can be summarized as follows:

TANGO×FIDELIO.

The seeds resulting from the above pollination were sown and plantlets were obtained which were physically and biologically different from each other. Selective study which was finalized on Jan. 15, 1989, at Santa Maria, Calif. resulted in the identification of a single plant of the new cultivar. This plant initially was designated BSF-100B.

It was found that the new cultivar of the present invention:

(a) exhibits attractive large semi-double salmon florets,
(b) forms attractive dark green foliage which resists breakdown during shipment,
(c) bears leaves which lack zoning, and
(d) exhibits an inherently compact and self-branching growth habit in the absence of growth regulators.

Older peduncles present on plants of the new cultivar after exposure to sunlight commonly assume the coloration of Red-Purple Group 59A.

Asexual reproduction of the new cultivar by vegetative cuttings initially taken on Feb. 10, 1989, and horticulturally examined in a controlled environment on Apr. 15, 1989, at Santa Maria, Calif., has demonstrated that the characteristics of the new cultivar as herein described are firmly fixed and are retained through successive generations of asexual propagation.

When plant material of the BSF-100B Dark Salmon cultivar is subjected to standard random amplified polymorphic DNA marker analysis (RAPD) using polymerase chain reaction (PCR) and a known unique set of DNA primers, it is found to exhibit a distinctive fingerprint map which is on file at the Ball Flora Plant Division of George J. Ball, Inc. at Arroyo Grande, Calif. BSR-100B Dark Salmon has not been observed under all possible environmental conditions to date. Accordingly, it is possible that the phenotype may vary somewhat with variations in the environment, such as temperature, light intensity, and day length.

When the new cultivar of the present invention is compared to the Eclipse Light Salmon cultivar, it is found that THE BSR-100B Dark Salmon cultivar exhibits a darker blossom coloration and a somewhat lighter foliage coloration as specified in greater detail hereafter. The peduncles tend to be Red-Purple Group 60A on the new cultivar and Red-Purple Group 59B on the Eclipse Light Salmon cultivar. Also, the foliage of the Eclipse Light Salmon cultivar exhibits a slight zone which tends to be absent on the BSR-100B Dark Salmon cultivar.

The new cultivar of the present invention is being marketed under the Showcase trademark.

BRIEF DESCRIPTION OF THE PHOTOGRAPH

The accompanying photographs show as nearly true as is reasonably possible in color illustrations of this color, typical plants and plant parts of the new cultivar. In some instances the Eclipse Light Salmon cultivar also is illustrated for comparative purposes.

Figure 1:
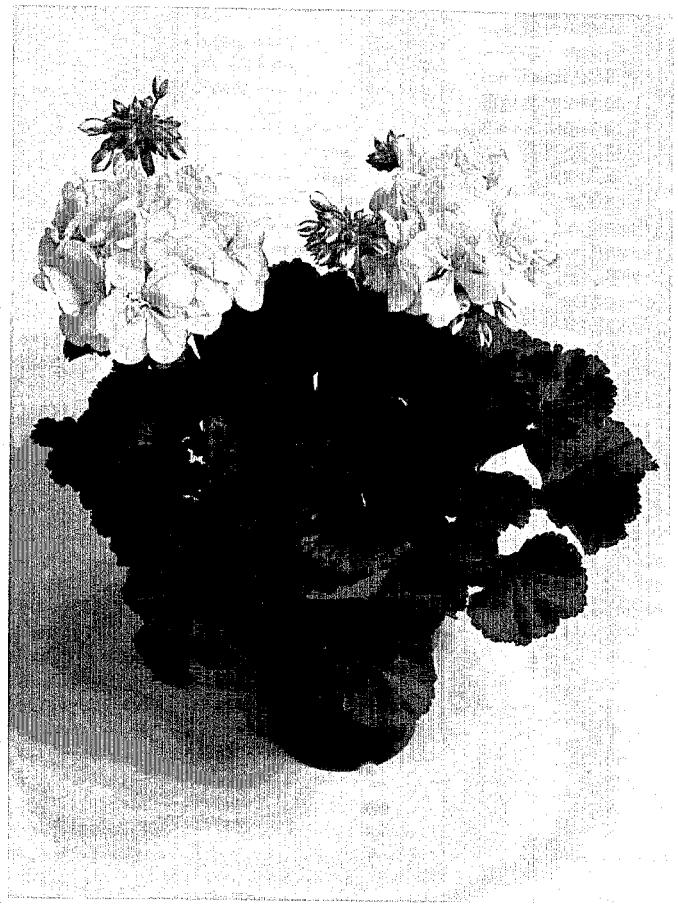
FIG. 1 illustrates a typical specimen of the overall plant of the new cultivar. The plant was grown in a greenhouse at Santa Maria, Calif.
Figure 2:
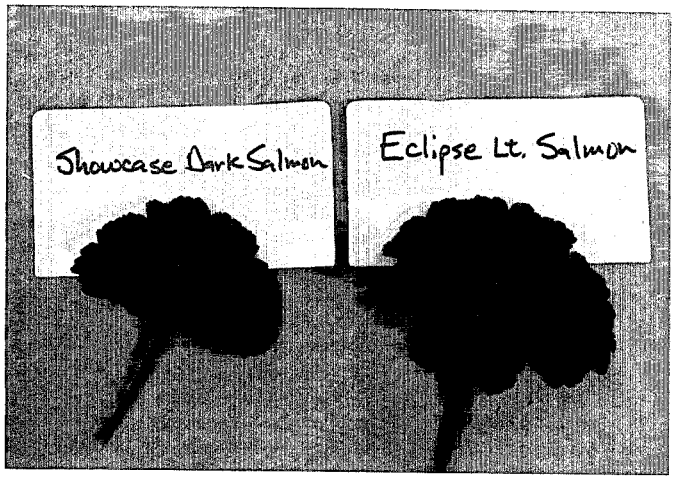
FIG. 2 illustrates for comparative purposes typical foliage of the new cultivar (left) and the Eclipse Light Salmon cultivar (right) obtained from plants growing in a greenhouse at Arroyo Grande, Calif., during October, 1992.
Figure 3:
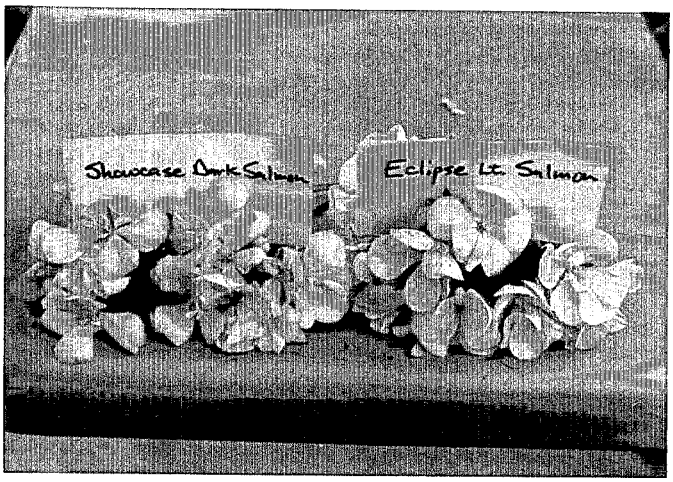

FIG. 3 illustrates for comparative purposes typical florets of the new cultivar (left) and the Eclipse Light Salmon cultivar (right) which were obtained from five month old plants growing in the field at Arroyo Grande, Calif. during October, 1992. Note that the florets of the BSR-100B Dark Salmon cultivar are larger and of a more bluish-salmon coloration while those of the Eclipse Light Salmon cultivar are of a more orange-salmon coloration.

Figure 4:
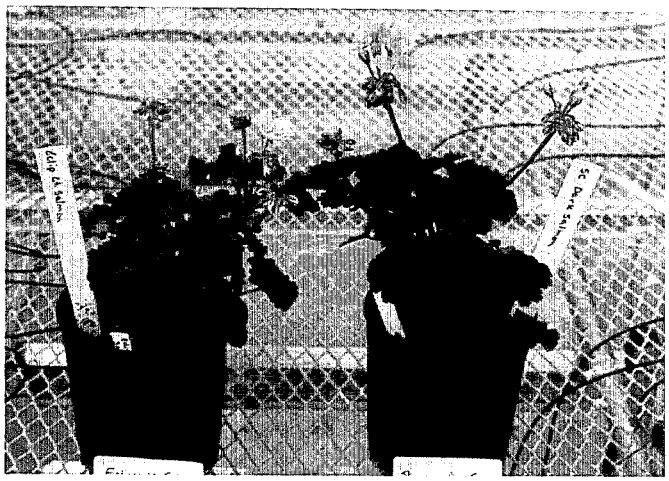

FIG. 4 illustrates for comparative purposes the growth habit and foliage of the BSR-100B Dark Salmon cultivar (right) and the Eclipse Light Salmon cultivar (left) when four months of age and growing in a greenhouse at Arroyo Grande, Calif. during October, 1992. Note that the foliage of the BSR-100B Dark Salmon cultivar is non-zoned while that of the Eclipse Light Salmon cultivar is zoned. Also, the growth habit of the BSR-100B Dark Salmon cultivar is shown to be more upright while that of the Eclipse Light Salmon cultivar is more compact and more mounded.

Figure 5:
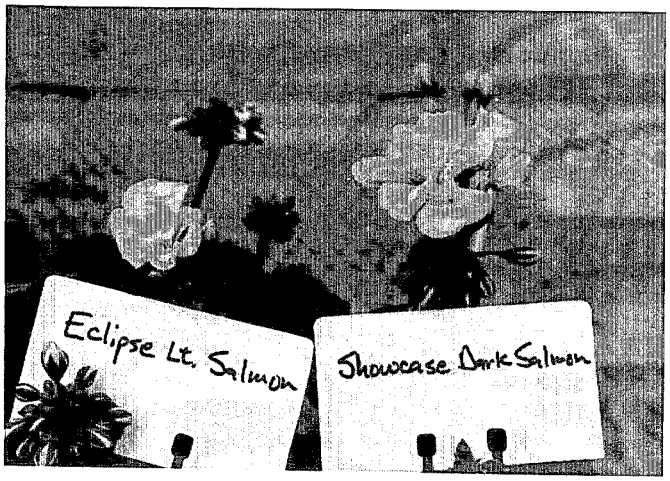

FIG. 5 illustrates individual florets of the plants of FIG. 4 with the BSR-100B Dark Salmon cultivar being shown on the right and Eclipse Light Salmon cultivar being shown on the left. Note that the floret coloration of the Eclipse Light Salmon cultivar is lighter and of a more orange-salmon coloration while that of the BSR-100B Dark Salmon cultivar is a darker salmon with blue overtones.

Figure 6:
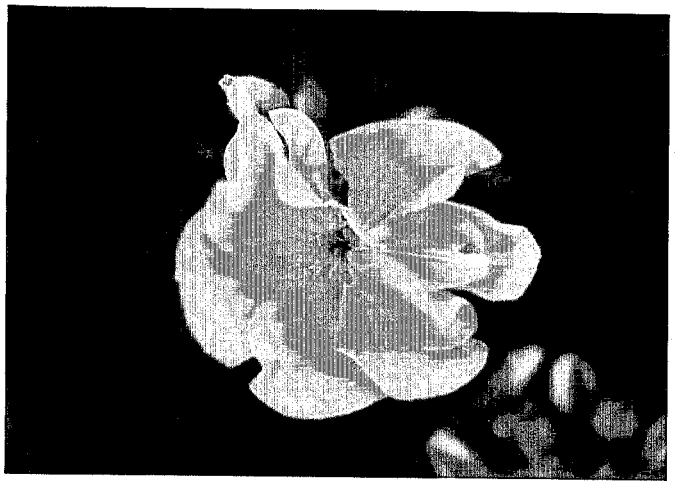

FIG. 6 illustrates for comparative purposes a closer view of a floret of the Eclipse Light Salmon cultivar. Such floret was obtained from the plant shown in FIGS. 4 and 5.

Figure 7:
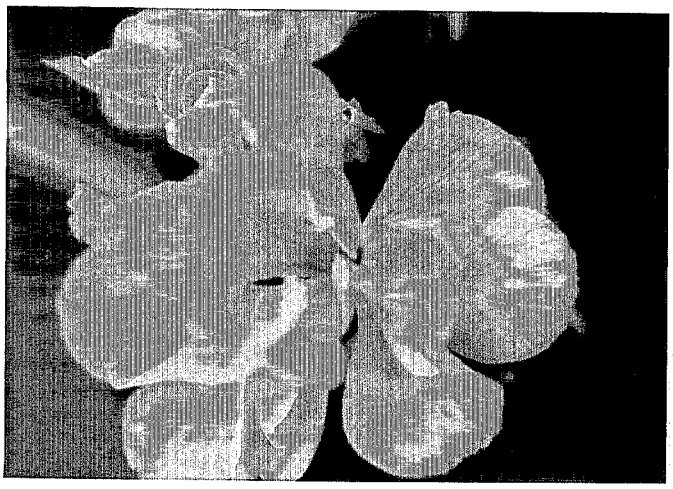

FIG. 7 illustrates a closer view of a larger floret of the BSR-100B Dark Salmon cultivar. Such floret was obtained from the plant shown in FIGS. 4 and 5.

DETAILED DESCRIPTION

The chart used in the identification of colors described herein is The R.H.S. Colour Chart of The Royal Horticultural Society, London, England. Color terminology in common terms sometimes precedes the reference to The R.H.S. Colour Chart information. The color values were determined on Jul. 18, 1991 at 11:00 a.m. to 12:00 noon using a light intensity at 1450 foot-candles at Santa Maria, Calif. The plants described were grown under standard greenhouse conditions.

Classification:

*Botanical.*—*Pelargonium* × *hortorum*, cv. BSR-100B Dark Salmon.

*Commercial.*—Zonal Geranium.

INFLORESCENCE

A. Umbel:

*Average diameter.*—Approximately 11 cm.

*Average depth.*—Approximately 6 cm.

*Peduncle length.*—Approximately 15 to 17 cm.

*Pedicel length.*—Approximately 2.5 to 3 cm.

When grown in a 4 inch pot at 12 weeks after the sticking of a bare root cutting, the BSR-100B cultivar commonly possesses approximately 4.25 umbels per plant on average, and the Eclipse Light Salmon cultivar commonly possesses approximately 2.5 umbels per plant on average. When five month old plants are grown in the field, the BSR-100B Dark Salmon cultivar commonly possesses approximately 50 to 55 umbels per plant while the Eclipse Light Salmon cultivar commonly possesses approximately 35 to 40 umbels per plant. Such field grown plants commonly possess approximately 35 to 39 florets per umbel for the BSR-100B Dark Salmon cultivar and approximately 41 to 45 florets per umbel for the Eclipse Light Salmon cultivar.

B. Corolla:

*Average diameter.*—Approximately 5.0 to 6.0 cm. This can be compared to approximately 4.5 to 4.75 cm. for the Eclipse Light Salmon cultivar.

*Form.*—Semi-double.

The florets of the BSR-100B Dark Salmon cultivar commonly possess approximately 5 to 8 large non-imbricate outer petals which measure approximately 3 cm. in length and approximately 1.8 cm. in width, and approximately 1 to 9 smaller inner petaloids which commonly measure in length from approximately 0.1 to 1.8 cm. In contrast the florets of the Eclipse Light Salmon cultivar commonly possess approximately 5 medium-sized imbricate outer petals which measure approximately 2.2 cm. in length and approximately 1.6 to 2 cm. in width, and approximately 5 to 7 smaller inner petaloids of varying size.

*Color (general tonality from a distance of* 3 *meters*).—Red Group 48B to 48C.

*Color (abaxial).*—Red Group 48B to 48C. This compares to Red Group 49A for the Eclipse Light Salmon cultivar.

*Color (adaxial).*—Red Group 48B to 48C. This compares to Red Group 49D for the Eclipse Light Salmon cultivar.

C. Bud:

*Shape.*—Upright, in a hemispheroidal cluster.

*Color (abaxial).*—Red Group 41A.

*Color (adaxial).*—Red Group 41A.

D. Reproductive organs:

*Androecium.*—The anthers commonly are approximately 2 mm. in length. The pollen is red in coloration, Red Group 48A; and the filaments commonly are petaloid in nature.

*Gynoecium.*—The pistil length commonly is approximately 7 to 8 mm., there is a single stigma which commonly branches into 6 parts, and the style length is approximately 4 to 5 mm. and its coloration approximates Red Group 43B.

*Fertility.*—Commonly does not produce fruits in the absence of mechanical fertilization.

E. Spring flowering response period: Approximately 6 to 7 weeks from rooted cuttings under greenhouse conditions maintained at 55° F. at night and 72° F.

during the day when potted on March 1st in a soil mix (e.g., Sunshine No. 2 brand soil mix) in 10 cm. pots.

F. Outdoor flower production: Vigorous and freely flowering under outdoor growing conditions with substantially continuous blooming.

G. Durability: The foliage coloration does not break down during shipping. Also, good tolerance to wind and rain is exhibited.

PLANT

A. Foliage: Non-zoned. In contrast the Eclipse Light Salmon cultivar is distinctly zoned.

*Form.*—Reniform, cordate base.

*Margin.*—This can be compared to the more crenate margin of the Eclipse Light Salmon cultivar.

*Color (abaxial).*—Dark green, Green Group 137A. This compares to Green Group 136B and Green Group 139A on the zoned foliage of the Eclipse Light Salmon cultivar.

*Color (adaxial).*—Dark green, Green Group 137B, having veins of Green Group 137D. This compares to Green Group 137B for the Eclipse Light Salmon cultivar.

B. General Appearance and form:

*Internode length.*—Commonly varies from approximately 2 to 3 cm.

*Branching pattern.*—Compact and self-branching. No pinching is required to obtain such self-branching.

*Height.*—Approximately 20 to 25 cm. above a 10 cm. pot when the blossoms first open. The plant is more upright than the Eclipse Light Salmon cultivar which exhibits a more compact and mounded growth habit.

I claim:

1. A new and distinct cultivar of Geranium plant named BSR-100B Dark Salmon, substantially as herein shown and described, which:

(a) exhibits attractive large semi-double salmon florets,
(b) forms attractive dark green foliage which resists breakdown during shipment,
(c) bears leaves which lack zoning, and
(d) exhibits an inherently compact and self-branching growth habit in the absence of growth regulators.

* * * * *